United States Patent [19]

Hagne

[11] Patent Number: 4,871,311

[45] Date of Patent: Oct. 3, 1989

[54] IMPROVEMENTS IN A METHOD OF AND A RETRACTION CORD FOR UNCOVERING AND DRAINING THE PREPARATION LIMIT LINE OF TEETH

[76] Inventor: Leif Hagne, Compognapark a, CH-7430 Thusis, Switzerland

[21] Appl. No.: 125,317

[22] Filed: Nov. 25, 1987

[51] Int. Cl.$^4$ ............................................... A61C 5/14
[52] U.S. Cl. ..................................... 433/136; 433/215
[58] Field of Search ................ 433/136, 138, 139, 215

[56] References Cited

U.S. PATENT DOCUMENTS

| | | | |
|---|---|---|---|
| 4,321,038 | 3/1982 | Porteous | 433/136 |
| 4,366,206 | 12/1982 | Tanaka | 428/364 |
| 4,465,462 | 8/1984 | Ticknor | 433/136 |
| 4,609,584 | 9/1986 | Cutler et al. | 604/383 |
| 4,650,479 | 3/1987 | Insley | 604/358 |

FOREIGN PATENT DOCUMENTS 3027958 2/1982 Fed. Rep. of Germany ...... 433/136

Primary Examiner—John J. Wilson
Attorney, Agent, or Firm—Cushman, Darby & Cushman

[57] ABSTRACT

A retraction cord is provided for use in uncovering and draining the preparation limit line of a tooth where the tooth emerges from gum tissue which is subject to bleeding during the course of conducting a procedure such as the taking of a dental impression, the cementing of a crown and the performance of conservative caries therapy. Practicing the method includes inserting said cord in a gingival crevice extending perimetrically of a tooth having a preparation limit line, where the tooth emerges from gum tissue, between the tooth and the gum tissue, and permitting the cord to absorb moisture so that the cord swells and thereby mechanically uncovers said preparation limit line and mechanically compresses said gum tissue, tending to stop bleeding of such gum tissue. The preferred material for making the cord is a superabsorbent swelling material made of an acrylic fiber having a skin constituted by a copolymer of polyacrylic acid and polyammonium acrylate and a core of polyacrylonitrile, in which the skin provides about thirty percent of the weight of the fiber.

10 Claims, 1 Drawing Sheet

IMPROVEMENTS IN A METHOD OF AND A RETRACTION CORD FOR UNCOVERING AND DRAINING THE PREPARATION LIMIT LINE OF TEETH

BACKGROUND OF THE INVENTION

This invention relates to a method of uncovering and draining the preparation limit line of teeth in conjunction with the taking of impressions, cementing and conservative caries therapy by the aid of a retraction cord. The invention also provides a new and improved retraction cord for this purpose.

When taking an impression, for example, after preparation of a tooth for a crown or a bridge, it is necessary in almost every case to uncover the preparation limit line to obtain an optimal fit of the tooth substitute. To obtain such a fit, cords are currently used, which are soaked in diverse astringent solutions, such as adrenalin, aluminum chloride etc. Such a cord is pressed down into the gingival crevice between the tooth and the gum tissue and will uncover by its pressure the preparation limit line of the tooth. Due to the fact that the cord is soaked in an astringent, solution any bleeding will be checked. The drawbacks associated with the retraction cords currently used are several. To be capable, at all, of being pressed down between the tooth and the gum tissue, it must not be too thick, which will restrict the uncovering of the preparation limit line. The cord is saturated with an astringent solution. By reason of the risk of general side effects, not more than 7 centimeters of adrenalin-soaked cord should be used in every instance, which might prove necessary, however, in larger dental reconstruction works. Many cords in current use untwist when pressed down into the gingival crevice, which will render the application difficult; this is tedious and irritating and will risk the impression quality.

SUMMARY OF THE INVENTION

By this invention, all the abovementioned drawbacks have been eliminated. A retraction cord is provided for use in uncovering and draining the preparation limit line of a tooth where the tooth emerges from gum tissue which is subject to bleeding during the course of conducting a procedure such as the taking of a dental impression, the cementing of a crown and the performance of conservative caries therapy. Practicing the method includes inserting said cord in a gingival crevice extending perimetrically of a tooth having a preparation limit line, where the tooth emerges from gum tissue, between the tooth and the gum tissue, and permitting the cord to absorb moisture so that the cord swells and thereby mechanically uncovers said preparation limit line and mechanically compresses said gum tissue, tending to stop bleeding of such gum tissue. The preferred material for making the cord is a superabsorbent swelling material made of an acrylic fiber having a skin constituted by a copolymer of polyacrylic acid and polyammonium acrylate and a core of polyacrylonitrile, in which the skin provides about thirty percent of the weight of the fiber.

BRIEF DESCRIPTION OF THE DRAWINGS

The invention will be described in greater detail with reference to the drawing, in which.

DETAILED DESCRIPTION

Figure 1:
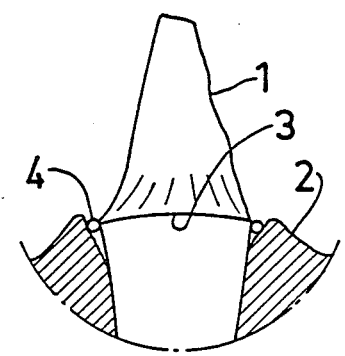
FIG. 1 illustrates in a general manner a prepared tooth with an applied retraction cord.

In the drawing, numeral 1 denotes a tooth, prepared e.g., for a crown (not shown). Numeral 2 denotes the tissue around the tooth, i.e. the gum tissue.

For instance, when taking impressions after preparing for the crown, the prepared tooth 1 including the preparation limit line 3 must stay clear of fluid and humidity, and the preparation limit line must stay uncovered.

Figure 2:
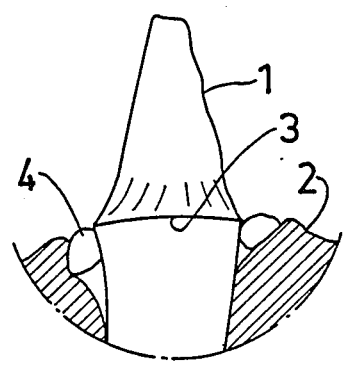
FIG. 2 depicts the same assembly as is shown in FIG. 1, but after the retraction cord has swelled.

To uncover the preparation limit line 3, a retraction cord 4 is accordingly pressed down around the tooth into the gingival crevice between the tooth 1 and the gum tissue 2. The superabsorbent cord will be subjected thereby to humidity—saliva, blood, water—and, according to the invention, the cord 4 will swell and increase its volume substantially, as illusstrated in FIG. 2. The cord 4 will then press the gum tissue 2 aside mechanically, as clearly seen from FIG. 2, and will stop any bleeding of the gum tissue by compressing the latter. Due to it having swelled by its contact with the fluid, the cord 4 will also uncover the preparation limit line mechanically at the same time as surrounding fluid is absorbed by the cord. The preparation limit line thereby can be kept dry.

The retraction cord 4 according to the invention should be made of a superabsorbent material that will increase its volume substantially to attain the effects aimed at, and can, for example, be manufactured of fibers sold under the trademark Lanseal F ®, by the firm Japan Exlan Co. Ltd., Osaka, Japan. Lanseal F fibers comprise a skin part (30% in wt) of copolymer of poly acrylic acid and a poly ammonium acrylate and core part (70% in wt) of a copolymer of poly acrylonitril. In this connection, reference is made to US-A-4 366 206 and US-A-4 374 175. In cord made of these fibers, the fiber length and diameter is 51 millimeters and 7 denier, respectively. The swelling properties are caused by three main factors, i.e. comprising a loosely cross-linked electrolyte water-soluble polymer with an ionic radical, outbreak of osmotic pressure due to the difference of ion concentration between the outside and the inside of the polymer and spreading of molecules due to the ionic repulsion of the high molecular electrolyte. The standard capacity is 150 ml(pure water)/g fibers. If available, cords manufactured of other fibers than these and having the specifically sought-after properties can, of course, be used instead. To be named as another example is fibers "KKF" manufactured and sold by Asahi Chemical Co., Japan, with teh absorbency capacity of 65 ml(pure water/g fibers).

Figure 3:
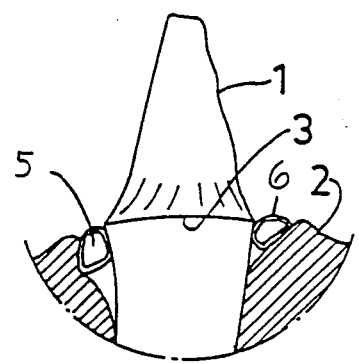
FIG. 3 is a view similar to FIG. 2, of a modified embodiment.

By choosing the fiber length and an appropriate twisting or spinning method, a cord can be manufactured having the properties that are of a decisive importance to the invention. One example of this cord according to the invention is a braided cord made up of four strands, two warp strands and two filling strands, the filling strands successively passing over and then under the two warp strands and the warp strands successively passing over and then under the two filling strands, in a per se known manner. A cord according to the invention could also be manufactured from superabsorbent nonwoven sheets made of the fibers concerned. The cord is cut from the sheet in long thin stripes. The cord may consist solely of the fluid superabsorbent and swelling fibers, these fibers in combination with e.g. cotton fibers or other fibers, or the cord can be in the shape of an expansible stocking 5 (FIG. 3) which surrounds a cord core 6 consisting of the abovementioned fibers. The stocking material can be synthetic fibers, cotton, nonwoven, or combinations thereof and spun in any per se known way to get an expansible stocking. This cord and/or stocking can, although not necessarily, be impregnated with a hemostatic, which may be appropriate in cases with more profuse bleedings.

When the core or cord swells upon growing moist, the stocking will become expanded. Due to this, an accelerated swelling effect is attained, as the fluid will increasingly easily penetrate through the stocking. The thickness of the stocking fabric can further be made with different measures, depending on the length of time required for applying the cord which in its turn depends on the treatment conditions. If the stocking fabric is very thin, the cord will begin to swell almost immediately on its contact with fluid. If the stocking fabric is thick it will require a longer time. Normally, it is desirable for a time delay of about 1 minute for applying the cord; therefore the thickness of the stocking fabric can, for instance, be made to suit this time.

By providing the cord with the above-described spun-around, elastic stocking, the cord will receive a mechanical resistance which will facilitate the insertion of the cord into the gingival crevice with, e.g., a packing instrument.

I claim:

1. A method for uncovering and draining the preparation limit line of a tooth where the tooth emerges from gum tissue which is subject to bleeding during the course of conducting a procedure such as the taking of a dental impression, the cementing of a crown and the performance of conservative caries therapy, said method comprising:
(a) providing a retraction cord made at least in part of an externally accessible superabsorbent swelling material; and
(b) inserting said cord in a gingival crevice extending perimetrically of a tooth having a preparation limit line, where the tooth emerges from gum tissue, between the tooth and the gum tissue, and permitting the cord to absorb moisture so that the cord swells and thereby mechanically uncovers said preparation limit line and mechanically compresses said gum tissue, tending to stop bleeding of such gum tissue.

2. The method of claim 1, wherein:
said superabsorbent swelling material constitutes a core of said cord, and said cord, as provided in step (a), further includes an expansible stocking surrounding said core.

3. The method of claim 2, wherein:
said stocking acts in step (b) to temporally-retard penetration of the moisture into said core.

4. The method of claim 2, wherein:
said stocking surrounding said cord, as provided in step (a), includes a hemostatic substance impregnated therein.

5. The method of claim 1, wherein:
said cord, as provided in step (a), is made of woven fibers.

6. The method of claim 1, wherein:
said cord, as provided in step (a), is made of nonwoven fibers.

7. The method of claim 1, wherein:
said superabsorbent swelling material of said cord, as provided in step (a), is made of acrylic fiber, such fiber having a skin constituted by a copolymer of polyacrylic acid and polyammonium acrylate and a core of polyacrylonitrile, in which the skin provides about thirty percent of the weight of the fiber.

8. A retraction cord for use in uncovering and draining the preparation limit line of a tooth where the tooth emerges from gum tissue which is subject to bleeding during the course of conducting a procedure such as the taking of a dental impression, the cementing of a crown and the performance of conservative caries therapy, by inserting a cord in a gingival crevice extending perimetrically of a tooth having a preparation limit line, where the tooth emerges from gum tissue, between the tooth and the gum tissue, and permitting the cord to absorb moisture so that the cord swells and thereby mechanically uncovers said preparation limit line and mechanically compresses said gum tissue, tending to stop bleeding of such gum tissue, said retraction cord comprising:
an elongated body of superabsorbent swelling material made of acrylic fiber, such fiber having a skin constituted by a copolymer of polyacrylic acid and polyammonium acrylate and a core of polyacrylonitrile, in which the skin provides about thirty percent of the weight of the fiber.

9. The retraction cord of claim 8, wherein:
said elongated body constitutes a core of said cord, and said cord futher includes an expansible stocking surrounding said cord.

10. The retraction cord of claim 9, wherein:
said expansible stocking includes a hemostatic substance impregnated therein.

* * * * *